(12) United States Patent
Kajitani et al.

(10) Patent No.: US 6,785,574 B2
(45) Date of Patent: Aug. 31, 2004

(54) MYOELECTRIC FEATURE-PATTERN CLASSIFICATION METHOD AND APPARATUS

(75) Inventors: Isamu Kajitani, c/o Nat'l. Inst. of Advanced Industrial Science and Tech,. AIST Tsukuba Center 2, 1-1-1, Umezono, Tsukuba-shi (JP), 305-8568; Tetsuya Higuchi, c/o Nat'l. Inst. of Advanced Industrial Science and Tech,. AIST Tsukuba Center 2, 1-1-1, Umezono, Tsukuba (JP), 305-8568

(73) Assignees: National Institute of Advanced Industrial Science and Technology, Tokyo (JP); Isamu Kajitani, Tsukuba (JP); Tetsuya Higuchi, Tsukuba (JP)

( * ) Notice: Subject to any disclaimer, the term of this patent is extended or adjusted under 35 U.S.C. 154(b) by 101 days.

(21) Appl. No.: 10/057,954

(22) Filed: Jan. 29, 2002

(65) Prior Publication Data

US 2002/0152186 A1 Oct. 17, 2002

(30) Foreign Application Priority Data

Jan. 30, 2001 (JP) .................................. 2001-020881

(51) Int. Cl.[7] ............................................... A61B 5/04
(52) U.S. Cl. ..................................................... 600/546
(58) Field of Search .......................... 600/546; 706/13, 706/14; 700/213, 250; 623/24, 58, 63, 25, 57; 375/316

(56) References Cited

U.S. PATENT DOCUMENTS 5,376,128 A * 12/1994 Bozeman, Jr. ............... 623/24
6,272,479 B1 * 8/2001 Farry et al. ................... 706/13
2002/0136328 A1 * 9/2002 Shimizu ....................... 375/316

OTHER PUBLICATIONS

I. Kajitani, et al., Technical Report of IEICE, PRMU98–86, vol. 98, No. 275, pp. 9–16, "Developing Adaptable EMG Controlled Prostheses to Disabled People", Sep. 18, 1998 (with English abstract).

* cited by examiner

Primary Examiner—Mary Beth Jones
Assistant Examiner—Brian Szmal
(74) Attorney, Agent, or Firm—Oblon, Spivak, McClelland, Maier & Neustadt, P.C.

(57) ABSTRACT

A feature-pattern extraction apparatus uses a logarithmic transformation processing to extract a feature pattern from a myoelectric pattern that is a muscle action potential. The extracted feature patterns are classified, and an output control signal is generated. By using the logarithmic transformation processing to extract feature patterns, distribution bias is reduced, improving classification accuracy.

6 Claims, 6 Drawing Sheets

The muscle contraction scheme

An example of sampled myoelectric signals

An example of the rectified myoelectric signals

MYOELECTRIC FEATURE-PATTERN CLASSIFICATION METHOD AND APPARATUS

BACKGROUND OF THE INVENTION

1. Field of the Invention

The present invention relates to a myoelectric feature-pattern classification method and apparatus in a method of interfacing muscle action potential (myoelectric pattern).

2. Description of the Prior Art

FIG. 2 is a drawing used to illustrate a prior-art apparatus that manipulates a control target by extracting a feature pattern from a myoelectric pattern and classifying the extracted feature pattern. In the drawing, ① denotes myoelectric patterns, ② a surface electrode group, ③ amplification and smoothing apparatuses, ④ a feature-pattern extraction apparatus, ⑤ a pattern classifier, and ⑥ control target such as a motor, a robot, a device for the disabled, a rehabilitation device, a myoelectric arm prosthesis, a game, and so forth.

As shown in the drawing, a myoelectric pattern ① that is an action potential generated by the coordinated action of a plurality of muscles, is measured by a set or a plurality of sets of surface electrode groups ② on a skin surface. What is measured is the sum of the action potentials generated by the plurality of muscles.

Next, the measured potential is subjected to amplification and smoothing by the amplification and smoothing apparatuses ③ The feature-pattern extraction apparatus ④ extracts a feature pattern from the amplified, smoothed signal. The pattern classifier ⑤ classifies feature patterns from the extracted signal, and generates control signals to control the control target ⑥. A real value filter, such as a neural network or the like, or a logical value filter, such as a logic circuit or the like, can be used for the pattern classifier.

This type of prior-art apparatus requires, as the feature-pattern extraction apparatus, a high-level arithmetic processing device (a high-specification CPU or DSP, or a special LSI) for FFT calculations and the like and for solving inverse mapping problems, which has been a problem standing in the way of reducing the size and cost of the apparatus. This has prevented the apparatus coming into widespread use as a myoelectric pattern interface.

Sometimes a bias in myoelectric pattern distributions can make it difficult to achieve classification with good accuracy. It is possible that the bias in the distribution is caused by the distance relationship between the measurement electrodes and contracted muscle. That is, because a myoelectric pattern at the contraction of a muscle that is far from the electrodes is attenuated as it passes through the living body tissue, it distributes in low-value regions. In contrast to this, in the case of the contraction of a muscle that is close to the electrodes, there is little attenuation from the propagation in the body, so it distributes in high-value regions.

The present invention is proposed to resolve the above problems, and has as an object to provide a myoelectric feature-pattern classification method and apparatus that is smaller and cheaper, promoting the wider use of a myoelectric interface apparatus.

Another object of the present invention is to provide a myoelectric feature-pattern classification method and apparatus that, in cases where the myoelectric pattern distribution is biased, can reduce the distribution bias and increase the pattern classification accuracy.

SUMMARY OF THE INVENTION

The myoelectric pattern classification method of the present invention comprises using logarithmic transformation processing to extract a feature pattern from a myoelectric pattern that is a muscle action potential, classifying the extracted feature pattern and generating an output control signal.

Also, the myoelectric pattern classification apparatus of the present invention comprises a feature-pattern extraction apparatus that uses a logarithmic transformation apparatus to extract a feature pattern from a myoelectric pattern that is a muscle action potential, and a pattern classifier that classifies the extracted feature pattern and generates an output control signal.

The distance relationship between a contracted muscle and the electrodes can give rise to distributions that are biased towards low-value regions and high-value regions. In this case, it is possible to decrease the distribution bias and raise pattern classification accuracy by using logarithmic transformation to transform the patterns to increase the low-value region resolution and decrease the high-value region resolution.

The above logarithmic transformation can be realized by means of an analogue filter, or by software on a CPU or microprocessor, or by a lookup-table or the like. This makes it possible to reduce the size and cost, thereby promoting the wider use of a myoelectric interface apparatus.

Other objects and features of the invention will be more apparent from the following detailed description of the invention based on the accompanying drawings.

DESCRIPTION OF THE PREFERRED EMBODIMENT

Figure 1:
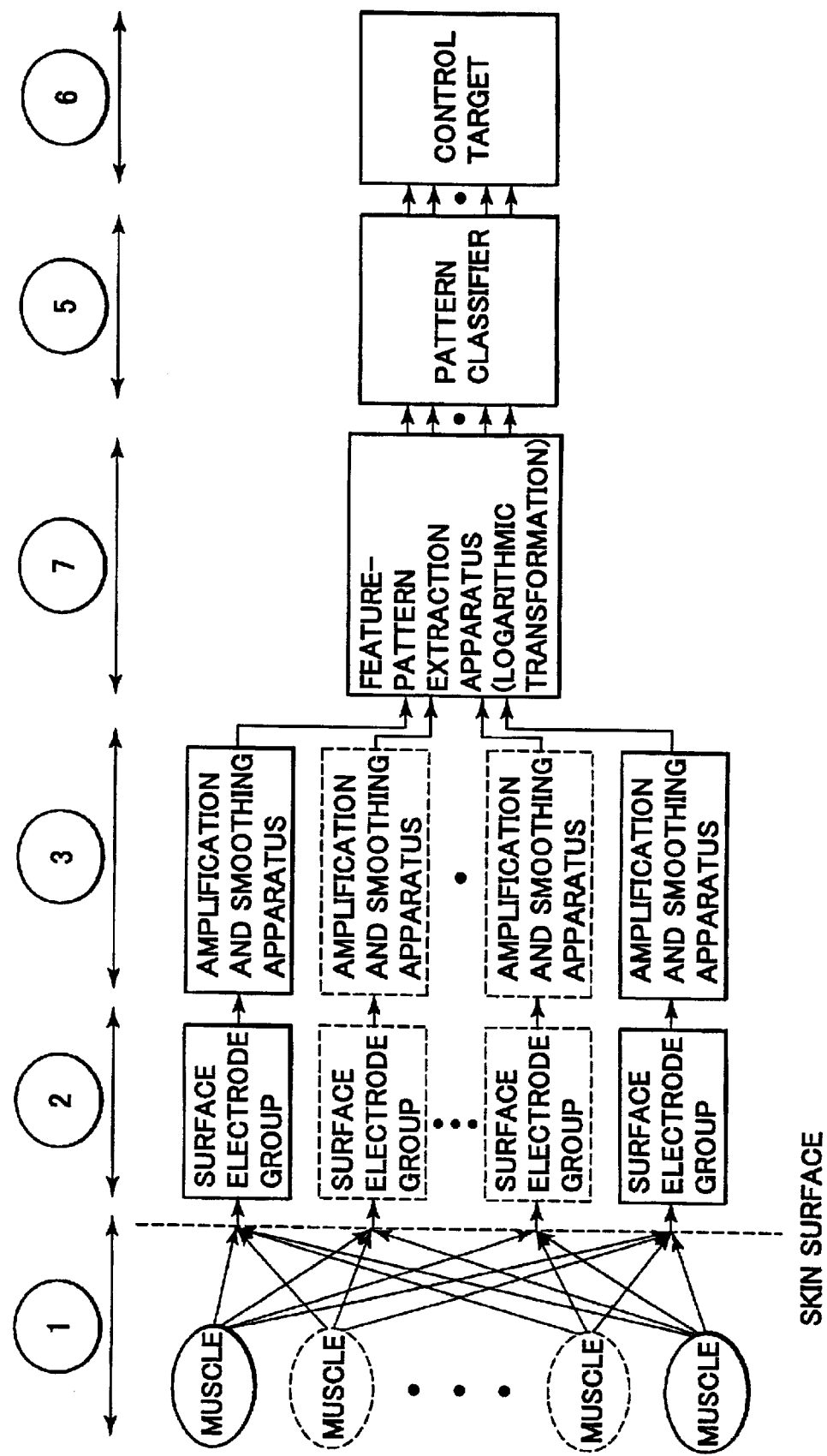
FIG. 1 is an explanatory drawing of the configuration of a myoelectric feature-pattern classification apparatus according to the present invention.
Figure 2:
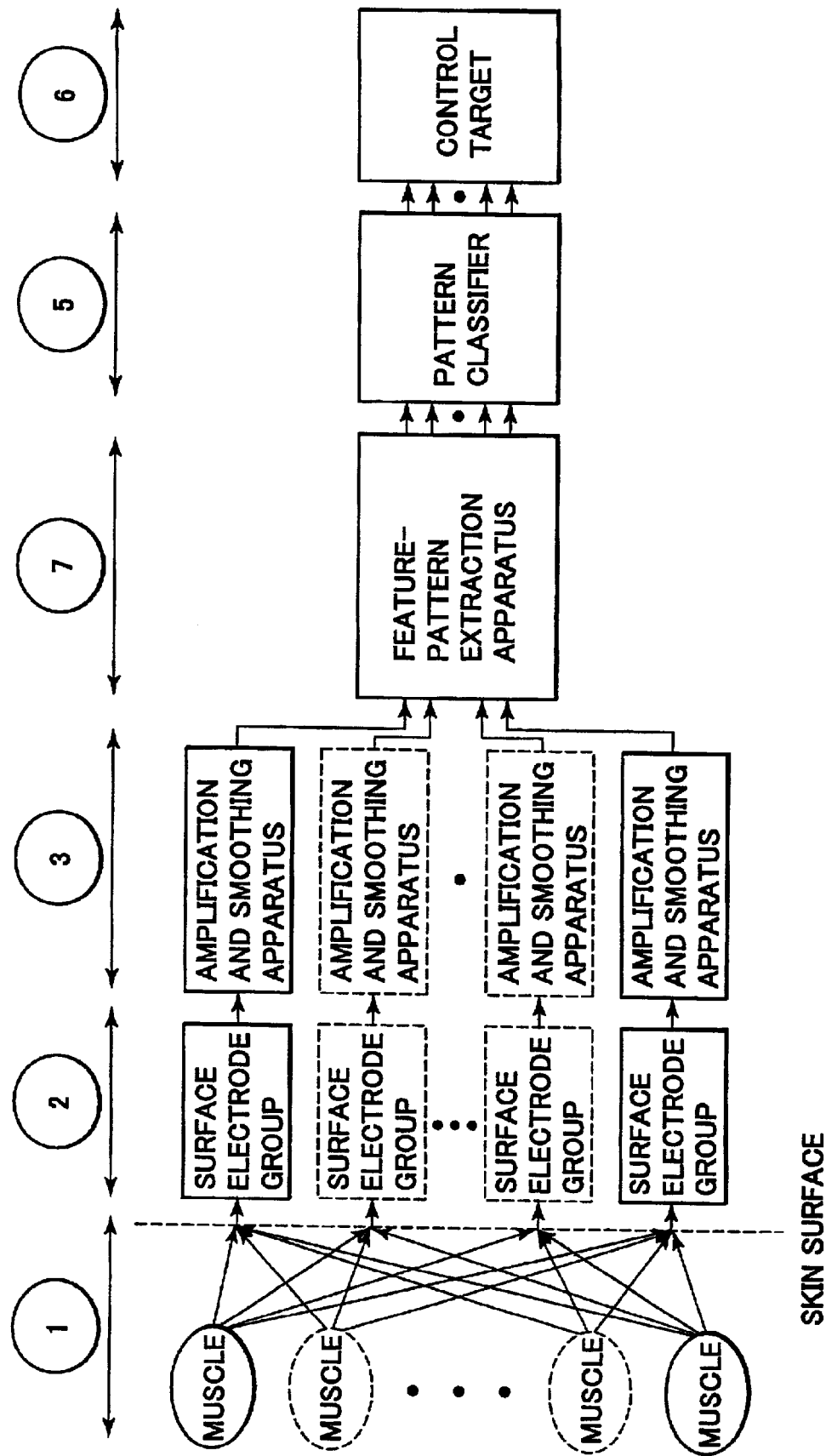
FIG. 2 is an explanatory drawing of the configuration of a myoelectric feature-pattern classification apparatus according to the prior art.

FIG. 1 is an explanatory drawing of the configuration of an apparatus of the present invention that extracts a feature pattern from myoelectric patterns and controls the motors used to operate an arm prosthesis as the control target ⑥. In the drawing, ① denotes myoelectric patterns, ② a surface electrode group, ③ amplification and smoothing apparatuses, ⑦ a feature-pattern extraction apparatus that uses a logarithmic transformation apparatus, ⑤ a pattern classifier, and ⑥ the control target.

As shown in the drawing, a myoelectric pattern ① that is an action potential generated by the coordinated action of a plurality of muscles is measured by one or a plurality of surface electrode groups ② on a skin surface. What is measured is the sum of the action potentials generated by the plurality of muscles. Next, the measured potential is subjected to amplification and smoothing by the amplification and smoothing apparatuses ③.

The present invention uses a logarithmic transformation apparatus as the feature-pattern extraction apparatus ⑦. The logarithmic transformation apparatus extracts feature patterns by performing logarithmic transformation of the myoelectric patterns. This logarithmic transformation can be realized by means of an analogue filter, or by software on a CPU or microprocessor, or by a lookup-table or the like. The pattern classifier ⑤ classifies feature patterns from the extracted feature patterns, and generates signals to control the control target ⑥. A real value filter, such as a neural network or the like, or a logical value filter, such as a logic circuit or the like, can be used for the pattern classifier.

In order to show the effect of the present invention, there will now be explained an example in which classification accuracy is improved by using the method of the present invention in the action-decisions of a myoelectric arm prosthesis.

Figure 3:
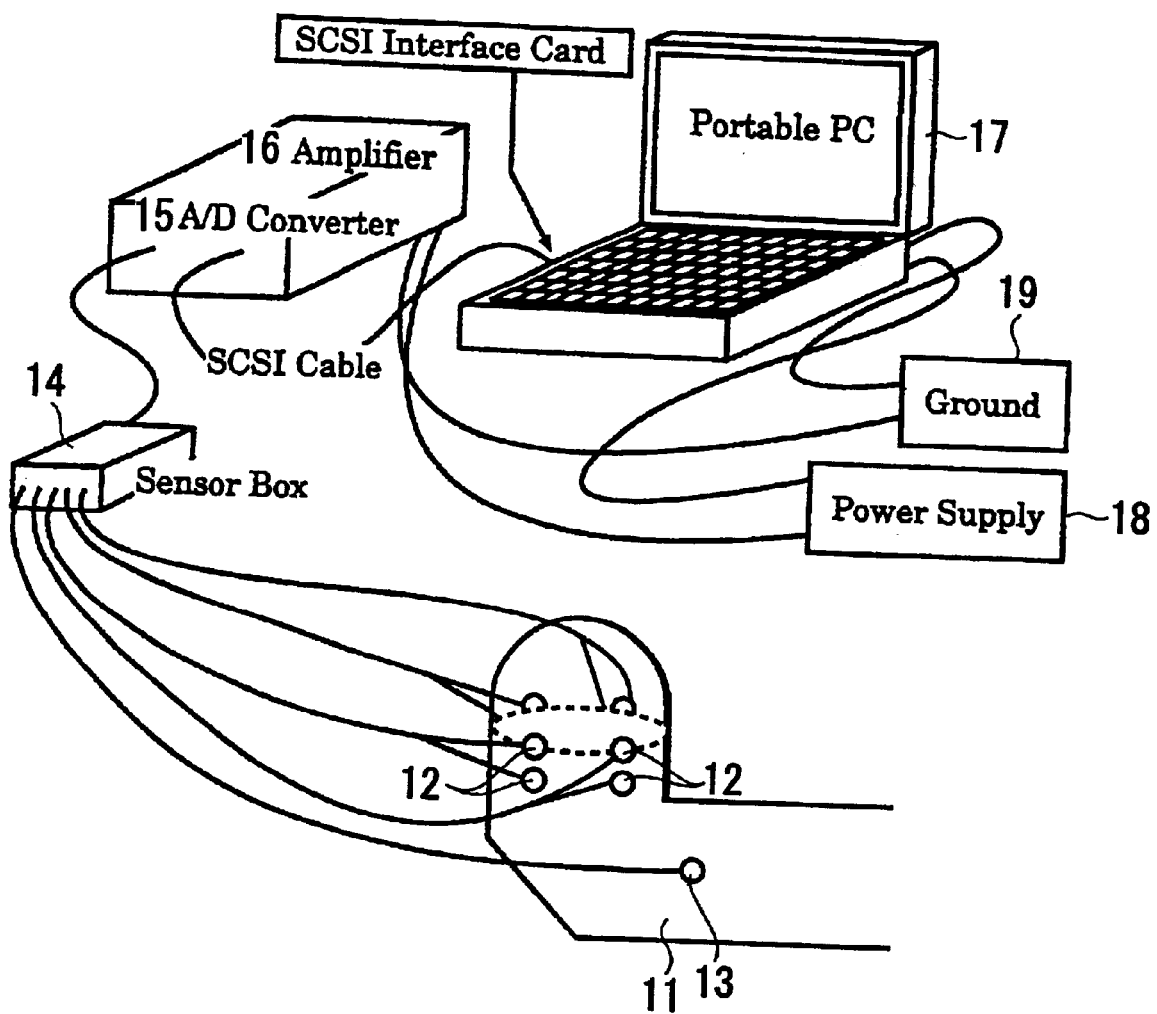
FIG. 3 is a general block diagram of an apparatus for measuring myoelectricity.

First, myoelectricity measurement will be described, using FIG. 3. Because the myoelectric signal is weak, in the order of several $\mu V$ to several mV, in the measurement thereof, it is generally necessary to subject a signal measured using two electrodes to differential amplification to reduce the effect of noise generated by power supplies or other electric devices. In the illustrated example, the myoelectricity measurement is made using eight (four sets) electrodes 12 applied to four locations around the forearm 11 of a myoelectric arm prosthesis. Reference numeral 13 denotes a reference electrode.

The weak myoelectric signals, measured by the four sets of electrodes 12 are sent, via a sensor box 14, to an amplifier 15 where they are differentially amplified and are then sent to an A/D converter 16. At the A/D converter 16, the amplified myoelectric signals are separated by 1000 Hz and converted into 12-bit digital signals and stored on a notebook type personal computer (PC) 17 connected by a SCSI interface. In the drawing, reference numeral 18 denotes a power supply and numeral 19 a ground. In this measurement, also, an analogue filter was used that blocks the commercial power supply frequency (50 Hz) in order to eliminate noise generated by the commercial power supply.

In the following explanation, equation 1 expresses a set of signals measured at time t.

$$f(t)=(f_1(t)f_2(t)f_3(t)f_4(t)) \quad \text{[Equation 1]}$$

Figure 4A:
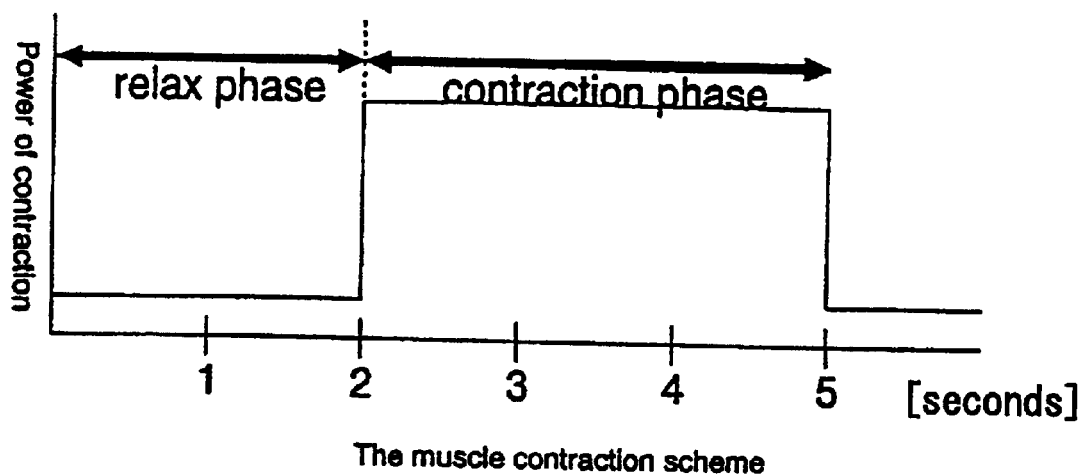
FIG. 4(a) is a graph showing the state of a muscle contracted for three seconds after being relaxed for two seconds.

Myoelectricity measurements were carried out while the muscles were contracted as if to perform six actions (forearm pronation, forearm supination, wrist flexion, wrist extension, hand closing and hand opening). That is, myoelectricity measurements were carried out while performing the muscle contractions shown in FIG. 4(a) (contracting the muscles after a two-second relaxation period and maintaining the contraction for three seconds) twenty times for each of the six actions (for a total of 120 times). In the case of forearm amputees, the myoelectricity measurements were carried out when the muscles were contracted based on a pre-amputation action image.

Figure 4B:
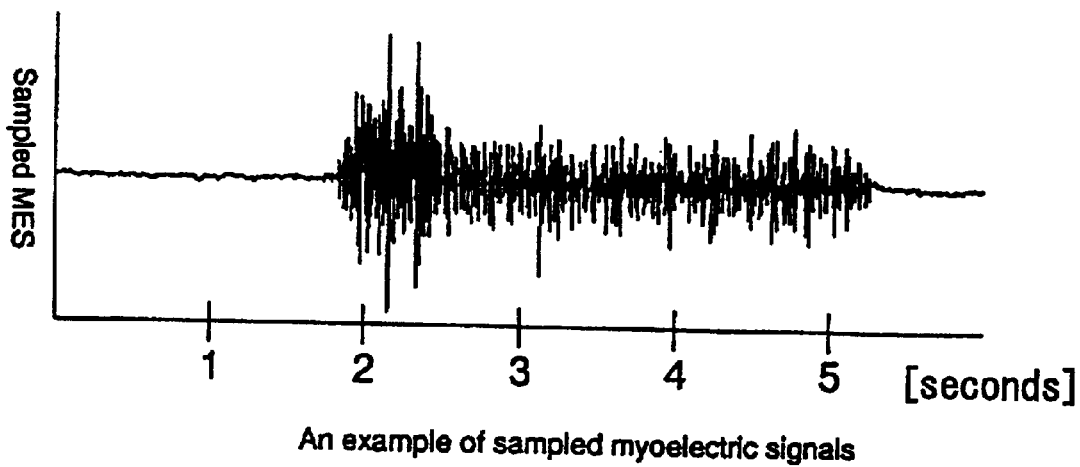
FIG. 4(b) is a graph showing an example of a myoelectric signal during, in the state of FIG. 4(a), wrist flexion.
Figure 4C:
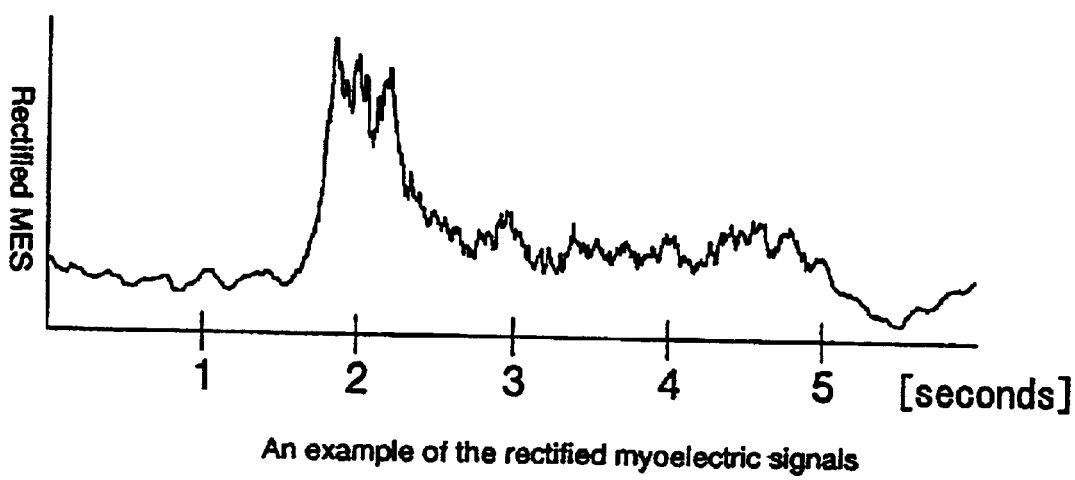
FIG. 4(c) is a graph showing an example of a myoelectric signal that is the myoelectric signal of FIG. 4(b) that has been subjected to smoothing processing.

FIG. 4(b) shows an example of myoelectricity measured on the surface of the skin over a flexed forearm muscle group during wrist flexion. The measured myoelectric signals were subjected to smoothing processing to remove high-frequency components. Such smoothing processing is usually done with an analogue low-pass filter. However, in the case of these measurements, storage on the PC was effected without using a low-pass filter to avoid loss of information, so the smoothing processing was carried out on the PC. Specifically, a smoothed rectified value at time t is obtained by the calculation shown in equation 2. FIG. 4(c) shows an example of a smoothed rectified myoelectric signal.

$$g(t) = \left( \sum_{i=1}^{100} |f_1(t-i)|, \sum_{i=1}^{100} |f_2(t-i)|, \sum_{i=1}^{100} |f_3(t-i)|, \sum_{i=1}^{100} |f_4(t-i)| \right) \quad \text{[Equation 2]}$$

Myoelectric feature patterns used in action-decisions of an arm prosthesis are usually extracted using (1) a method in which the extraction is made from the myoelectricity measured at the time of the initiation of the muscle contraction, or (2) a method in which the extraction is made from the myoelectricity measured during a state in which muscle contraction is maintained (hereinafter called the steady state). In the case of method (1), there is the advantage that the delay from the initiation of muscle contraction until the armprosthesis starts an action is short. However, with respect to the action classification rate, method (2) is known to be better than method (1), so here, the feature patterns are extracted using steady-state myoelectricity.

The feature patterns are extracted using smoothed, rectified steady-state myoelectric values. This smoothing is also usually carried out using an analogue low-pass filter, but here, the average value of the values obtained on the PC by equation 2 during a period of one second is calculated and used as the feature pattern.

Figure 5:
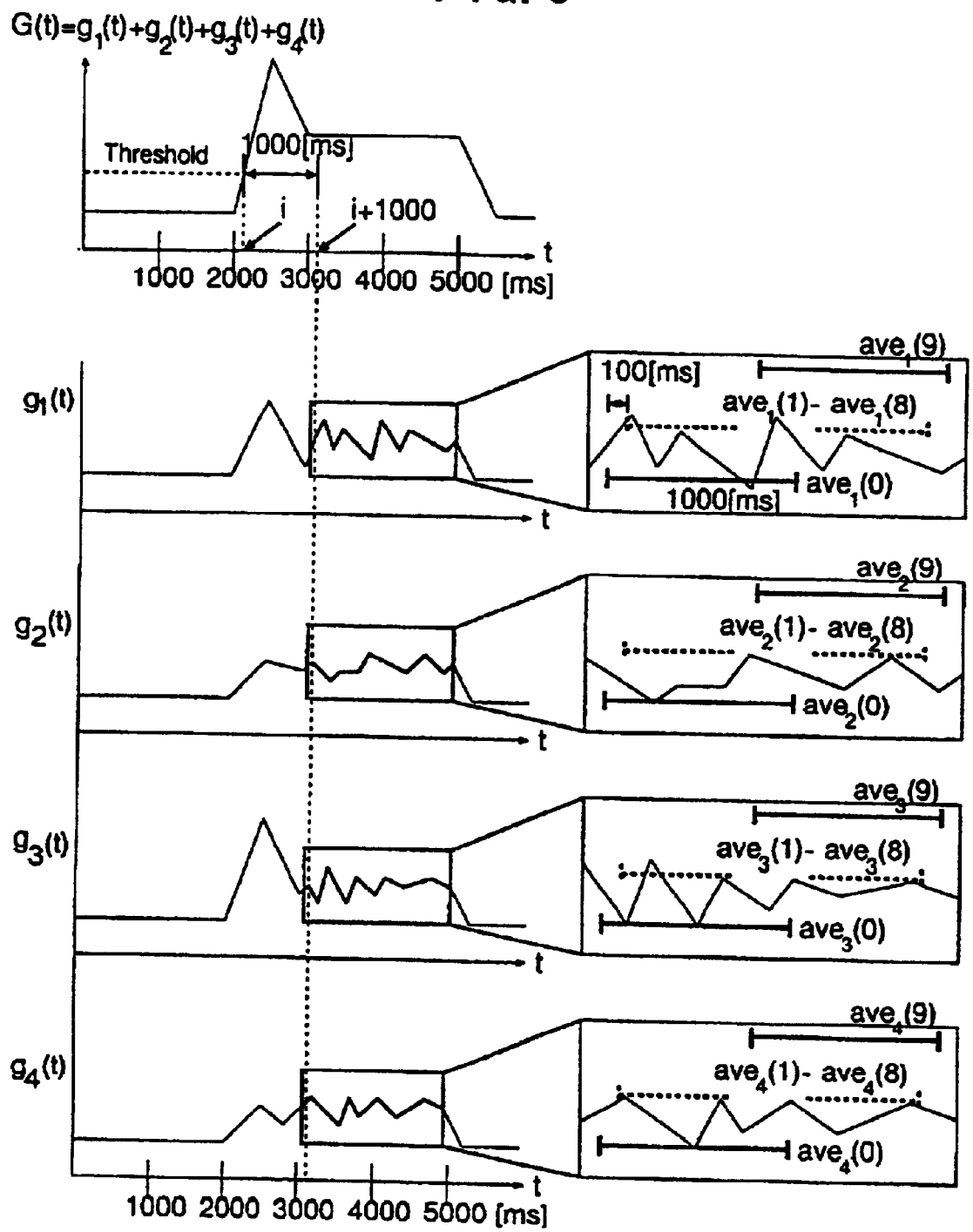
FIG. 5 is a drawing for explaining the feature-pattern extraction method.

In this feature-pattern extraction, in order to make it less tiring for the subject during the myoelectricity measurements, ten averaged values are obtained from one muscle contraction. That is, as shown in FIG. 5, averaged values per second, each offset 100 milliseconds starting from one second after action initiation, are obtained using the calculation shown in equation 3. Here, i is the time at which an action is initiated, that is, the time at which the value obtained by equation 4 exceeds a pre-set threshold value.

$$ave(n) = \frac{\sum_{j=1}^{1000} g(i+1000+j+n*100)}{1000} \quad \text{[Equation 3]}$$

$(n = 0, 1, \ldots, 9)$ $$G(t)=g_1(t)+g_2(t)+g_3(t)+g_4(t) \quad \text{[Equation 4]}$$

However, in practice, depending on how a muscle contracts, there are cases in which the value of equation 4 does not exceed the threshold value. Therefore, not all the twenty contractions per action can be used for the calculation of equation 3. Therefore, as training patterns for training the pattern classifier, equation 3 values are used from five of the muscle contractions in which the equation 4 value exceeded the threshold value (5 [muscle contractions]×10 [patterns]×6 [actions]=300 [patterns]). The equation 3 values extracted from another five muscle contractions are used as test patterns for evaluating the pattern classifier. In the following explanation, prepared training patterns are expressed by equation 5 and prepared test patterns are expressed by equation 6.

$$Tr_{org}(n)=(Tr_{org,1}(n),Tr_{org,2}(n),Tr_{org,3}(n),Tr_{org,4}(n))(n=0,\ldots,299) \quad \text{[Equation 5]}$$

$$Te_{org}(n)=(Te_{org,1}(n),Te_{org,2}(n),Te_{org,3}(n),Te_{org,4}(n))(n=0,\ldots,299) \quad \text{[Equation 6]}$$

Figure 6:
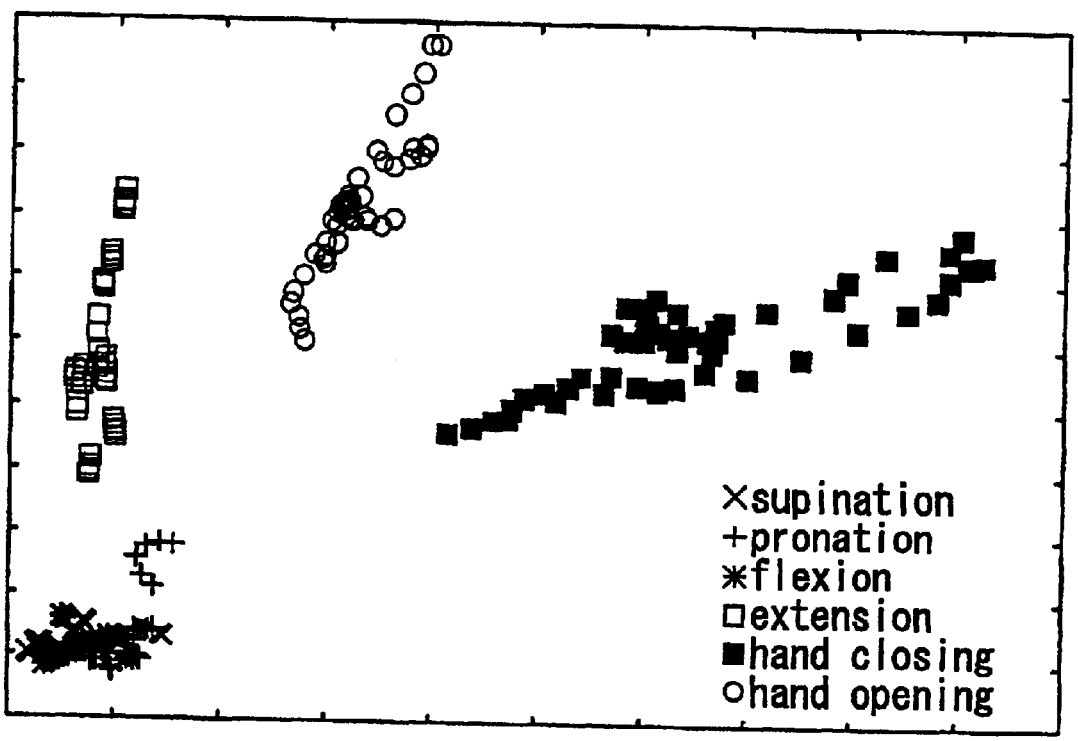
FIG. 6 is a diagram of the distribution of the myoelectric feature-pattern extraction method patterns.

Here, an investigation relating to the characteristics of myoelectric-pattern distributions will be followed by a discussion of a method that utilizes those characteristics to improve classification accuracy. To investigate the characteristics of myoelectric-pattern distributions, FIG. 6 shows a plot, for each action, in which the first components of the above-described training patterns are X axis values and the second components are Y axis values. In this example, it can be seen that the characteristics of the myoelectric-pattern distributions are broadly divided into two.

The first characteristic is that the myoelectric patterns do not distribute uniformly, but distribute with biases. That is, they distribute divided into low-value regions and high-value regions, with patterns having a distribution biased towards low-value regions (supination+, pronation×, flexion *) having a small distance between patterns of each action, and feature-patterns distributed in high-value regions (extension □, hand closing ■, hand opening ○) showing a large variance.

This distribution bias may be caused by the distance relationship between the measurement electrodes and the contracted muscles. That is, because a myoelectric pattern at the time of the contraction of a muscle that is far from the electrodes is attenuated as it passes through the living body tissue, it distributes in low-value regions. In contrast to this, in the case of the contraction of a muscle that is close to the electrodes, there is little attenuation from the propagation in the body, so it distributes in high-value regions.

The following description relates to a method of improving classification accuracy by utilizing this characteristic to reduce bias in classification-pattern distributions. To do this, first, in order to evaluate classification-pattern distributions, there is obtained a "within-class variance between-class variance rate," which is usually used as an evaluation index. That is, in the usual pattern classification, high-accuracy classification is possible when patterns belonging to the same group (hereinafter called class) distribute closer together and patterns belonging to different classes distribute apart. Accordingly, the within-class distribution spread (within-class variance: Equation 7) between-class distribution spread (between-class variance: Equation 8) rate can be used as a distribution evaluation index.

$$\sigma_W^2 = \frac{1}{300}\sum_{i=1}^{6}\sum_{x\in\chi_i}(x-m_i)^t(x-m_i) \quad \text{[Equation 7]}$$

$X_i$: set of patterns belonging to the ith class,
$m_i$: average vector for $X_i$ $$\sigma_B^2 = \frac{1}{300}\sum_{i=1}^{6}50\times(m_i-m)^t(m_i-m) \quad \text{[Equation 8]}$$

$X_i$: set of patterns belonging to the ith class,
$m_i$: average vector for $X_i$,
m: average vector of all patterns Specifically, a higher within-class variance between-class variance rate, defined by equation 9, enables a feature pattern to be evaluated as better.

$$J_\sigma = \frac{\sigma_B^2}{\sigma_W^2} \quad \text{[Equation 9]}$$

In accordance with these equations, when the within-class variance between-class variance rate of the training pattern was obtained using equation 5, the average for 13 subjects was 0.48. Below, the logarithmic transformations shown next were used to carry out classification-pattern transformations with the aim of achieving high-accuracy classification of myoelectric patterns by improving the within-class variance between-class variance rate.

Here, in order to improve the characteristic of distances between patterns for each action being small in low-value regions and patterns distributed in high-value regions having a large variance, a method that performs logarithmic transformation is proposed. With this method, owing to the nature of logarithms, in low-value regions resolution is increased, and in high-value regions resolution is decreased.

Figure 7:
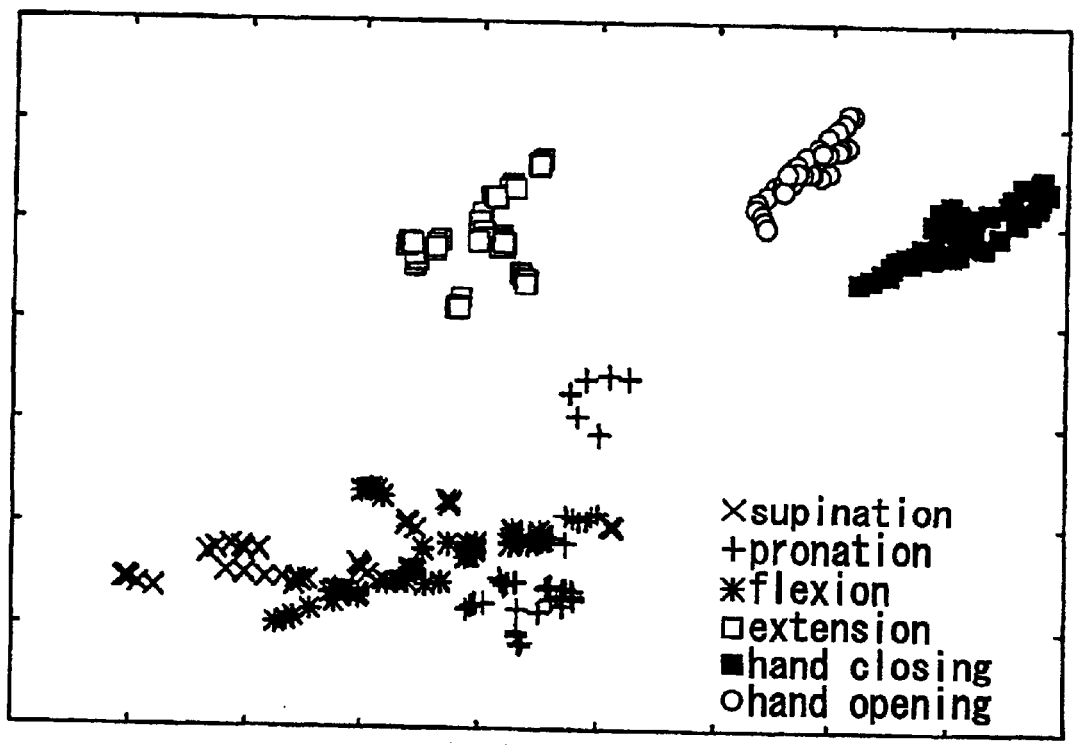
FIG. 7 is a diagram of the distribution of the myoelectric feature patterns that are the feature patterns of FIG. 6 that have been subjected to logarithmic transformation.

Accordingly, if, for example, the distribution shown in FIG. 6 is subjected to logarithmic transformation, as shown in FIG. 7, the variance of patterns distributed in high-value regions becomes lower, and the distance between patterns distributed in low-value regions becomes higher.

Thus, the calculations shown in equation 10 and equation 11 were used to perform logarithmic transformation on feature patterns. When the within-class variance between-class variance rate was obtained using equation 5, the average for the 13 subjects was 0.89. That is, relative to the case in which logarithmic transformation is not used, it was possible to achieve an approximately 1.85-fold improvement, so it can be expected that higher-accuracy classification will be possible.

$$\begin{aligned} Tr_{\log}(n) &= (Tr_{\log,1}(n),\ Tr_{\log,2}(n),\ Tr_{\log,3}(n),\ Tr_{\log,4}(n)) \\ &= (-\log(Tr_{org,1}(n)),\ -\log(Tr_{org,2}(n)),\ -\log(Tr_{org,3}(n)),\ -\log(Tr_{org,4}(n))) \\ &(n = 0, 1, \ldots, 299) \end{aligned} \quad \text{[Equation 10]}$$

-continued $$Te_{\log}(n) = (Te_{\log,1}(n), Te_{\log,2}(n), Te_{\log,3}(n), Te_{\log,4}(n))$$
$$= (-\log(Te_{org,1}(n)), -\log(Te_{org,2}(n)), -\log(Te_{org,3}(n)), -\log(Te_{org,4}(n)))$$
$$= (n = 0, 1, \ldots, 299)$$

[Equation 11]

In the following, training patterns obtained with equation 5 and equation 10 are each used to train the pattern classifier, and test patterns obtained with equation 6 and equation 11 are used to evaluate each classifier. In this evaluation, the pattern classifier is neural-network-based, and the freely distributed NevProp (Nevada back Propagation) is the neural network software package used. NevProp is a perceptron simulator that can be used extremely easily.

A feature of NevProp is its use of a method called cross-validation to prevent the phenomenon where the pattern classifier loses its generalization ability with respect to test patterns as a result of excess adaptation to the training patterns (hereinafter called overfitting). In this method, the training patterns are divided into two sets, which are used in training to enable correct classification of both without loss of generalization ability with respect to test patterns. NevProp also repeats the cross-validation five times to reduce the bias effect during the division of the training patterns.

The structure of the neural network used for the classification has four input-layer nodes, eight intermediate-layer nodes, and six output-layer nodes. The output-layer nodes correspond to the six prosthetic-arm actions, and when a threshold value (0.5) is exceeded, the corresponding action is selected.

The result of classification using this neural network showed that with the logarithmic transformation, the myoelectric-pattern classification ratio improved by an average of 2.7% with respect to thirteen subjects, and by a maximum of 23.5% (nine subjects).

The distance relationship between a contracted muscle and electrodes can give rise to myoelectric patterns distributed with biases towards low-value regions and high-value regions, in which case there is a problem of decreased classification accuracy. Using log arithmic transformation to transform patterns makes it possible to reduce the distribution bias by increasing the low-value region resolution and decreasing the high-value region resolution. This makes it possible to increase the pattern classification accuracy and, by also expanding the range of possible application, makes it possible to promote the wider use of a myoelectric interface apparatus. Also, this method can be realized by means of an analogue filter, or by software on a CPU or microprocessor, or by a lookup-table or the like, making it possible to reduce the size and cost.

What is claimed is:

1. A myoelectric pattern classification method comprising:
   extracting a feature pattern from a myoelectric pattern that is a muscle action potential using logarithmic transformation processing;
   classifying the extracted feature pattern; and
   generating an output control signal.

2. The myoelectric pattern classification method according to claim 1, wherein the extracted feature pattern is classified by one of a neural network and a logic circuit.

3. The myoelectric pattern classification method according to claim 1, wherein the extracted feature pattern is classified by one of a real value filter of a neural network and a logic value filter of a logic circuit.

4. A myoelectric pattern classification apparatus comprising:
   a feature-pattern extraction apparatus configured to use a logarithmic transformation apparatus to extract a feature pattern from a myoelectric pattern that is a muscle action potential; and
   a pattern classifier configured to classify the extracted feature pattern and to generate an output control signal.

5. The myoelectric pattern classification apparatus according to claim 4, wherein the pattern classifier comprises one of a neural network and a logic circuit.

6. The myoelectric pattern classification apparatus according to claim 4, wherein the pattern classifier comprises one of a real value filter of a neural network and a logic value filter of a logic circuit.

* * * * *